(12) United States Patent
Gass et al.

(10) Patent No.: US 6,907,768 B2
(45) Date of Patent: Jun. 21, 2005

(54) DEVICE FOR COUPLING A MICROCHROMATOGRAPH WITH A MASS SPECTROMETER AND ANALYSIS DEVICE

(75) Inventors: Jean-Louis Gass, St. Just Chaleyssin (FR); Ronan Cozic, Briis-sous-Forges (FR); Georges Ponchin, Meudon la Furt (FR)

(73) Assignees: Commissariat a l'Energie Atomique (FR); Centre National de la Recherche Scientifique (FR)

( * ) Notice: Subject to any disclaimer, the term of this patent is extended or adjusted under 35 U.S.C. 154(b) by 293 days.

(21) Appl. No.: 10/181,556

(22) PCT Filed: Nov. 29, 2001

(86) PCT No.: PCT/FR01/03760

§ 371 (c)(1),
(2), (4) Date: Jul. 19, 2002

(87) PCT Pub. No.: WO02/44710

PCT Pub. Date: Jun. 6, 2002

(65) Prior Publication Data

US 2004/0025566 A1 Feb. 12, 2004

(30) Foreign Application Priority Data

Nov. 29, 2000 (FR) .............................. 00 15415

(51) Int. Cl.[7] .................... G01N 30/72; G01N 30/06
(52) U.S. Cl. .................. 73/23.37; 73/23.42; 95/87; 96/106; 422/89
(58) Field of Search ..................... 73/23.35, 23.37, 73/23.42; 95/82, 87; 96/101, 106; 422/89

(56) References Cited

U.S. PATENT DOCUMENTS 4,662,914 A * 5/1987 Hansen et al. ............. 96/106

FOREIGN PATENT DOCUMENTS

WO    WO 97/23779    7/1997

OTHER PUBLICATIONS

XP–000993588 Henneberg, et al., "High–Performance Gas Chromatograph–Mass Spectrometer Interfacing: Investigation and Optimization of Flow and Temperature", Journal of Chromatography, 167, pp. 139–147 (1978).

XP–000993587 Henneberg, et al., "Special Techniques in the Combination of Gas Chromatography and Mass Spectrometry", Journal of Chromatography, 112, pp. 343–352 (1975).

Message, "Practical Aspects of gas chromatography/mass spectrometry", John Wiley & Sons ed., (1984) (abstract only).

* cited by examiner

Primary Examiner—Daniel S. Larkin
(74) Attorney, Agent, or Firm—Hutchison & Mason PLLC (57) ABSTRACT

A coupling device connecting the output of a microchromatograph ($\mu$CG) to the input of a mass spectrometer (MS), said coupling device comprising a capillary tube with one end connected in sealed fashion to the source under vacuum of the mass spectrometer through the intermediary of an interface device, and with the other end connected to the output of the microchromatograph, in slack fashion, open to the atmosphere; the length and the diameter of the capillary tube being chosen such that the flow rate inside the capillary tube is very close to the flow rate at the output from the microchromatograph; the interface device being, furthermore, provided with heating means for very precise adjustment of the flow rate registered by the capillary.

6 Claims, 9 Drawing Sheets

DEVICE FOR COUPLING A MICROCHROMATOGRAPH WITH A MASS SPECTROMETER AND ANALYSIS DEVICE

FIELD OF THE INVENTION

The invention relates to a coupling device between a microchromatograph and a mass spectrometer.

The invention also relates to an analysis device comprising a microchromatograph and a mass spectrometer connected through the intermediary of this coupling device.

BACKGROUND OF THE INVENTION

The combination of a gas chromatograph (GC) with a mass spectrometer (MS), possibly associated with a computer is one of the most powerful tools utilised in analytic chemistry and is, in particular, applied to analysis of gases.

Significant progress has been made in this technique, especially through the development of capillary columns in fused silica with small diameter and flow rate and the appearance of new mass spectrometers with high pumping capacity.

Thus, the microchromatograph ($\mu$CG) is an apparatus making it possible to carry out high resolution and high performance analysis of complex mixtures rapidly, for example in less than three minutes.

The detector is a non-destructive microkatharometer, which explains why it is of interest to couple the microchromatograph ($\mu$CG) with a mass spectrometer which adds the possibility of reliable identification of each component separated by the chromatographic column.

A significant problem of devices combining a chromatograph and a spectrometer relates to the choice of the coupling system forming the interface between the two apparatuses.

The problem of coupling varies according to the chromatographic device used and the pumping capacity of the spectrometer. The preceding generation of classic katharometers imposed the use of full columns, of large diameter, for example several millimeters, and a high vector gas flow, for example several tens of milliliters per minute. Coupling with a mass spectrometer then required a flux separator and differential pumping, always difficult to control [1].

The katharometer microdetector (microkatharometer) coupled to capillary columns with low flow rate (1 to 2 ml/min.) is now perfectly compatible with the pumping capacities of a state of the art mass spectrometer.

Direct on-line coupling without any separator is thus possible, nonetheless on the condition that it is ensured that a permanent load loss of one bar is maintained between the microdetector and the mass spectrometer source: this is the function ensured by a specially dimensioned capillary tube.

Assuming that this condition is satisfied, it is possible in practice to carry out the linking to the microdetector in two ways: either sealed, or open.

Figure 1:
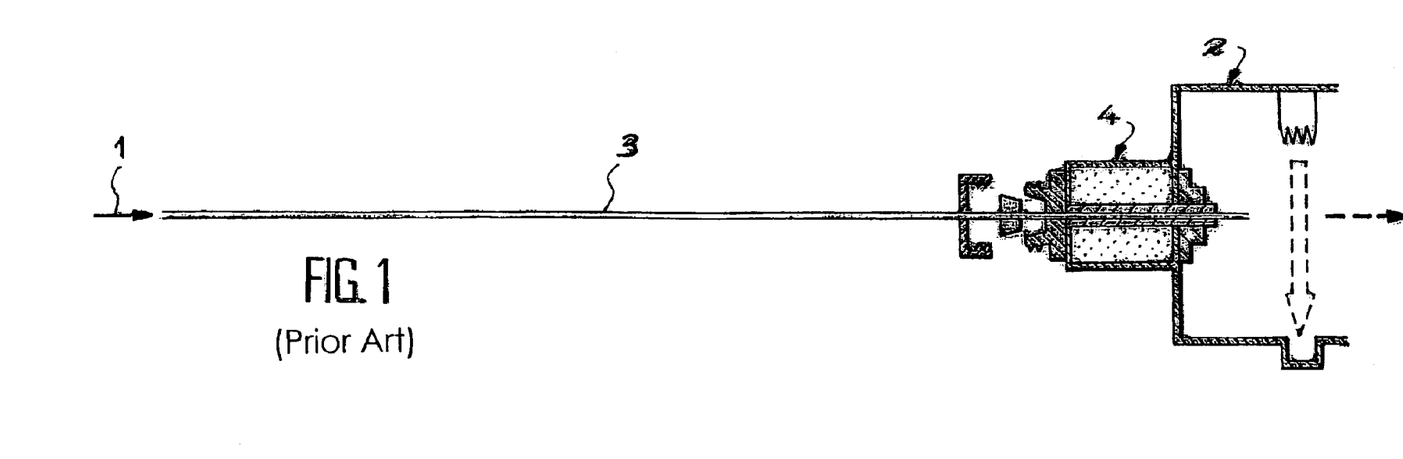
FIG. 1 is a diagrammatic cross-section showing an on-line coupling device, without separator, of the sealed coupling type, of prior art.

The sealed coupling is shown in FIG. 1. In this coupling the flow from the detector 1 arrives directly in the source 2 through the intermediary of the capillary tube 3 and the interface 4.

This coupling risks perturbing the operation of the microkatharometer detector, subject to a variation of the spectrometer pumping capacities or modifications of analysis conditions, in particular the head pressure and/or temperature of the column.

In other words, the sealed coupling has the advantage of a yield of 100%, but to the detriment of optimum operation of either the microkatharometer, which may be in depression, or the spectrometer, whose vacuum may become defective through saturation of its pumping capacities.

Figure 2:
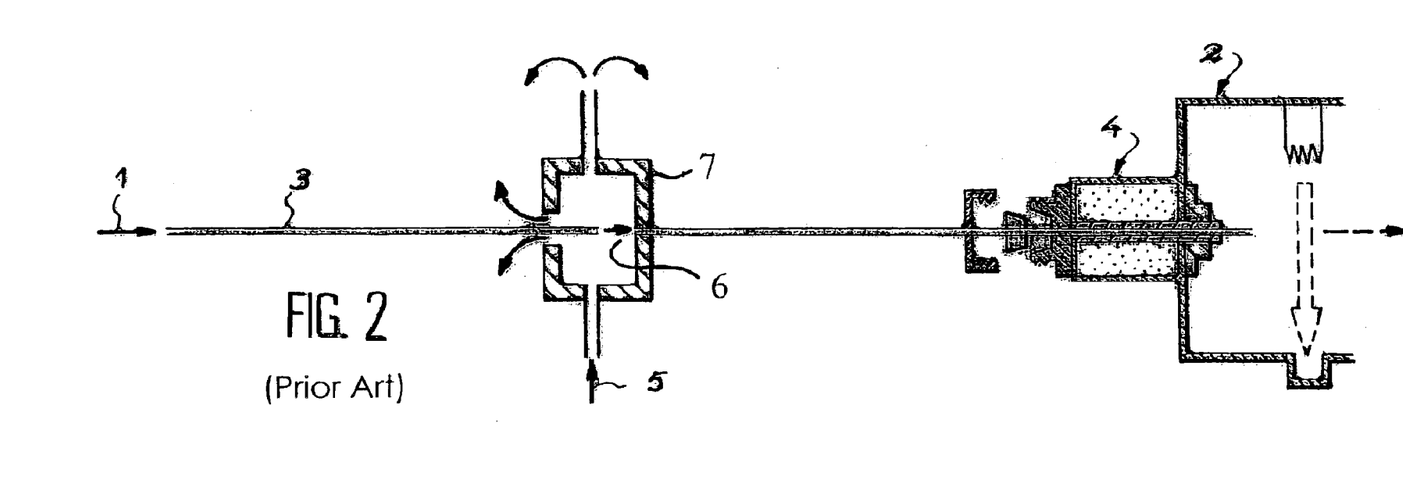
FIG. 2 is a diagrammatic cross-section showing an on-line coupling device, without separator, of the open coupling device type, of prior art.

On the other hand, the connection or open coupling 7, as shown in FIG. 2, has the advantage of preserving the optimum operational conditions of the two detectors, and the retention times are identical to those obtained in classic chromatography [2]. This mounting usually operates according to the following principle: the load loss of the transfer line is imposed, which is one bar, the diameter and the length of the capillary 3 being chosen in such a way that a vector gas flow close to the tolerable maximum for the spectrometer (source 2) crosses through the transfer line, and this flow rate is as close as possible to the flow leaving the microdetector [3].

The authors advise addition of helium 5 to compensate for a lowered flow rate, this helium protecting the mass spectrometer from air entry. This solution has the advantage of preserving both the mass spectrometer and the katharometer, but it introduces dilution of the solute flow 6, which can be a disadvantage in all cases where trace search is the required aim.

None of the coupling devices known in prior art provides satisfactory coupling between the output from the microchromatograph, that is the katharometer and the mass spectrometer source.

Such a coupling device must ensure several functions and fulfil several requirements, in particular the following:

to ensure operation of the katharometer detector at atmospheric pressure, whatever the analysis requirements relative, in particular, to the head pressure of the column and the temperature of the column.

This operation is the gauge of optimum sensitivity of the detector and the linearity of the response, in function of the concentration of species;

to register the totality of the flow leaving the microdetector and consequently to benefit from maximum detection sensitivity of the mass spectrometer;

to preserve the separation of the species already detected, and to transfer them to the spectrometer source, under high vacuum; and this coupling device must be able to be connected indiscriminately to any one of the modules, numbering four for example, able to equip the microchromatograph. The passage from one micro-detector to another must be very simple and rapid, without disturbing the operation of the spectrometer in any way.

SUMMARY OF THE INVENTION

The aim of the present invention is, among other things, to provide a coupling device which does not have the inconveniences, limitations, defects and disadvantages of prior art, and which solves the problems of coupling devices of prior art.

A further aim of the present invention is to provide a coupling device which, among other things, answers the criteria and requirements defined above for such a device.

This aim and further aims are achieved, according to the invention, by a coupling device connecting the output from a microchromatograph ($\mu$CG) to the input of a mass spectrometer (MS), said coupling device comprising a capillary tube with one end connected in sealed fashion to the source under vacuum of the mass spectrometer through the intermediary of an interface device, and with the other end connected to the output of the microchromatograph, in slack fashion, open to the atmosphere; the length and the diameter of the capillary tube being chosen such that the flow rate inside the capillary tube is very close to the flow rate at the output from the microchromatograph; the interface device being, furthermore, provided with heating means for very precise adjustment of the flow rate registered by the capillary.

The coupling device according to the invention, provided with a specific heating interface, ensures the transfer of solutes leaving the microdetector at atmospheric pressure towards the spectrometer source operating under high vacuum.

The coupling device according to the invention provides a solution to the problems posed by prior art coupling devices and fulfils the criteria and requirements described above.

The coupling according to the invention can be defined as an "open" coupling which, in particular, makes it possible to preserve both the mass spectrometer and the katharometer, while still conserving the integral solute flow, without any dilution.

For the first time, according to the invention, a coupling device exists connecting two detectors with fundamentally different operating principles, working on a common sample and whose detection limits are completely comparable.

In other words, the device according to the invention conserves the separation obtained in the microchromatograph integrally, and transfers it without changing it, nor diluting it, to the mass spectrometer.

During the chromatographic analysis, the flow rate in the column may change because of temperature variations.

According to the invention, the heating of the interface makes it possible to adjust the temperature to ensure continuity of the flow rate, which is absolutely impossible with prior art coupling devices.

According to the invention, the flow rate registered by the capillary tube is very easily adjusted by simple modification of the interface temperature.

Advantageously, the interface temperature is adjusted such that the flow rate registered by the capillary is very close to or equal to the flow rate at the output of the microchromatograph.

Advantageously, a comparison is made between the relative intensity of the peaks, on the one hand of water and, on the other hand, of nitrogen and/or oxygen present in the mass spectrometer source and measures are taken in consequence concerning the heating means of the interface in order to increase or reduce the temperature of the latter and to reduce or raise respectively the flow rate registered by the capillary tube.

The heating means, according to the invention, provided for the interface device make it possible to vary this temperature over a wide range, generally from the ambient temperature to 200° C.

This temperature depends on the capillary used (diameter and length). Within the range of temperatures above, for each capillary tube diameter there exists a range of preferred temperatures—for example 50 to 60° C.—within the temperature range above, for which the flow registered by the capillary is strictly equal to the output flow rate from the chromatographic column.

According to the invention, the temperature of the interface can be optimised for each chromatographic column temperature, and an adequate operating domain for coupling analysis can be determined for all circumstances.

The invention also relates to an analysis device comprising a microchromatograph and a mass spectrometer, the output from the microchromatograph being connected to the input of the mass spectrometer by the coupling device, such as described above.

Such an analysis device possesses all the advantages linked to the implementation of the coupling device according to the invention and, for the first time, it associates two detectors whose operating principles differ fundamentally, working with a common sample and whose detection limits are perfectly comparable.

According to the invention, the analysis device makes it possible to carry out two analyses with a single injection.

The analysis device, according to the invention, enables quantitative and qualitative analysis of unknown mixtures without it being necessary to possess the corresponding standard mixtures.

Advantageously, the analysis device according to the invention can be provided upstream from the microchromatograph by a pre-concentration or concentration, or restitution device, making it possible to accumulate the traces of compounds to be analysed in a fluid.

This pre-concentration device depends on absorption followed by thermo-desorption.

Advantageously, the analysis device according to the invention is a transportable device, particularly when it is provided with the pre-concentration system described above, which makes it possible to carry out analyses of traces.

The device according to the invention can be applied to all fields whether trace analysis is indispensable or not: the environment, refineries, storage and distribution of natural gas, confined atmosphere, reactor crown etc.

BRIEF DESCRIPTION OF THE DRAWINGS

The invention will be understood better by reading the following description, given as an illustrative and non-limiting example, with reference to the drawings attached, in which:

FIGS. 9A, 9B, 9C and 9D show the identification of unknown products present in mixtures in the trace state;

DETAILED DESCRIPTION OF THE PREFERRED EMBODIMENTS

The coupling device according to the invention connects the output from a microchromatograph ($\mu$CG) to the input of a mass spectrometer (MS), in particular a quadripole mass spectrometer.

Thus, this coupling associates two detectors depending on completely different analytic principles and operating from a same sample.

The coupling, carried out and tested successfully, is composed of three distinct elements, each having a precise function during the analysis:

- the microchromatograph makes the separation between the different constituents of the gaseous mixture. Each compound is detected by the microchrokatharometer, which leads to emission of a first chromatogram;
- the quadripole mass spectrometer makes it possible to obtain a second chromatogram based on the total ion current, together with the mass spectrum of each of the compounds, this spectrum providing identification; and
- the specific interface of the invention ensures the transfer of solutes leaving the microdetector at atmospheric pressure towards the spectrometer source operating under high vacuum.

In the following, each of the three elements is described.

Figure 3:
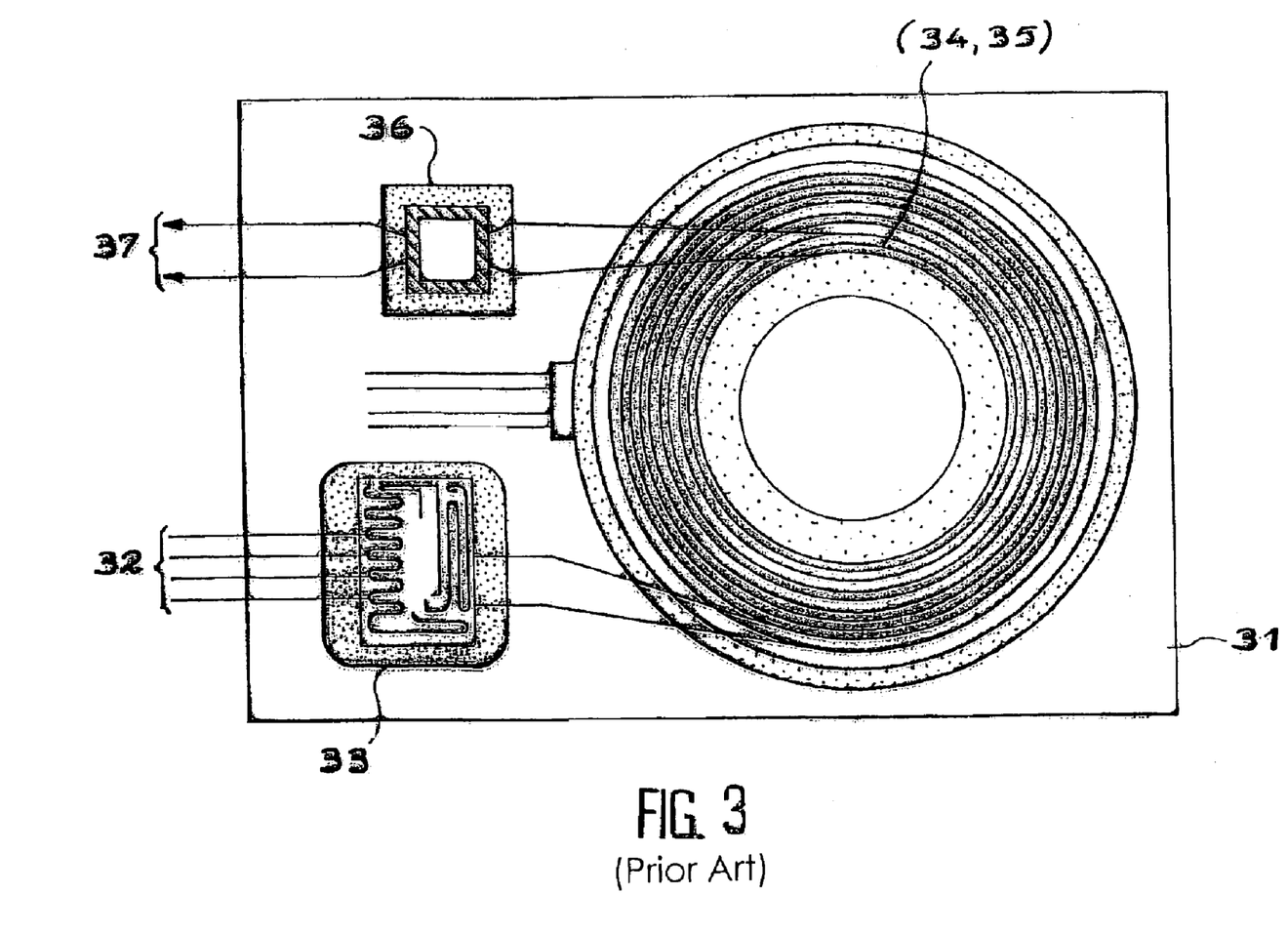
FIG. 3 is a diagrammatic view from above of a microchromatograph capable of being connected to a mass spectrometer by the coupling device according to the invention.

The first element is thus a microchromatograph; a particular microchromatograph will be described below, such as that marketed by the Société SRA INSTRUMENTS®, whose module is shown in FIG. 3, but it is very clear that the device according to the invention enables the coupling of all $\mu$CG before all MS.

The microchromatograph is a gas analyser of both rapid and high performance. The heart of the system is the analytic module constituted by an automatic injection valve, of the analysis column equipped with a heating device and detector of thermal conductivity, also called "microkatharometer".

The micro-CG is normally equipped with two to four chromatographic modules 31, each of these modules alone being a chromatograph with its own detector and capable of operating with its vector gas. It is possible to adjust the head pressure and the column temperature (isothermic), the length of time of analysis and also the volume injected.

A membrane micro-pump, for example common to the two modules, is capable of sucking a sample as long as its pressure is at the neighbouring minimum, for example 600 mbar (absolute pressure) and can withstand a suction pressure reaching, for example, four bar.

The automatic injector 33, specific to each module, receives the samples in 32 and makes it possible to introduce programmable volumes of samples comprised, for example, between 0.33 and 15 $\mu$l in the columns. Associated with the capillary or micro-capillary columns, the ensemble as a whole enables very short analysis times, for example from 30 to 160 seconds.

Figure 10:
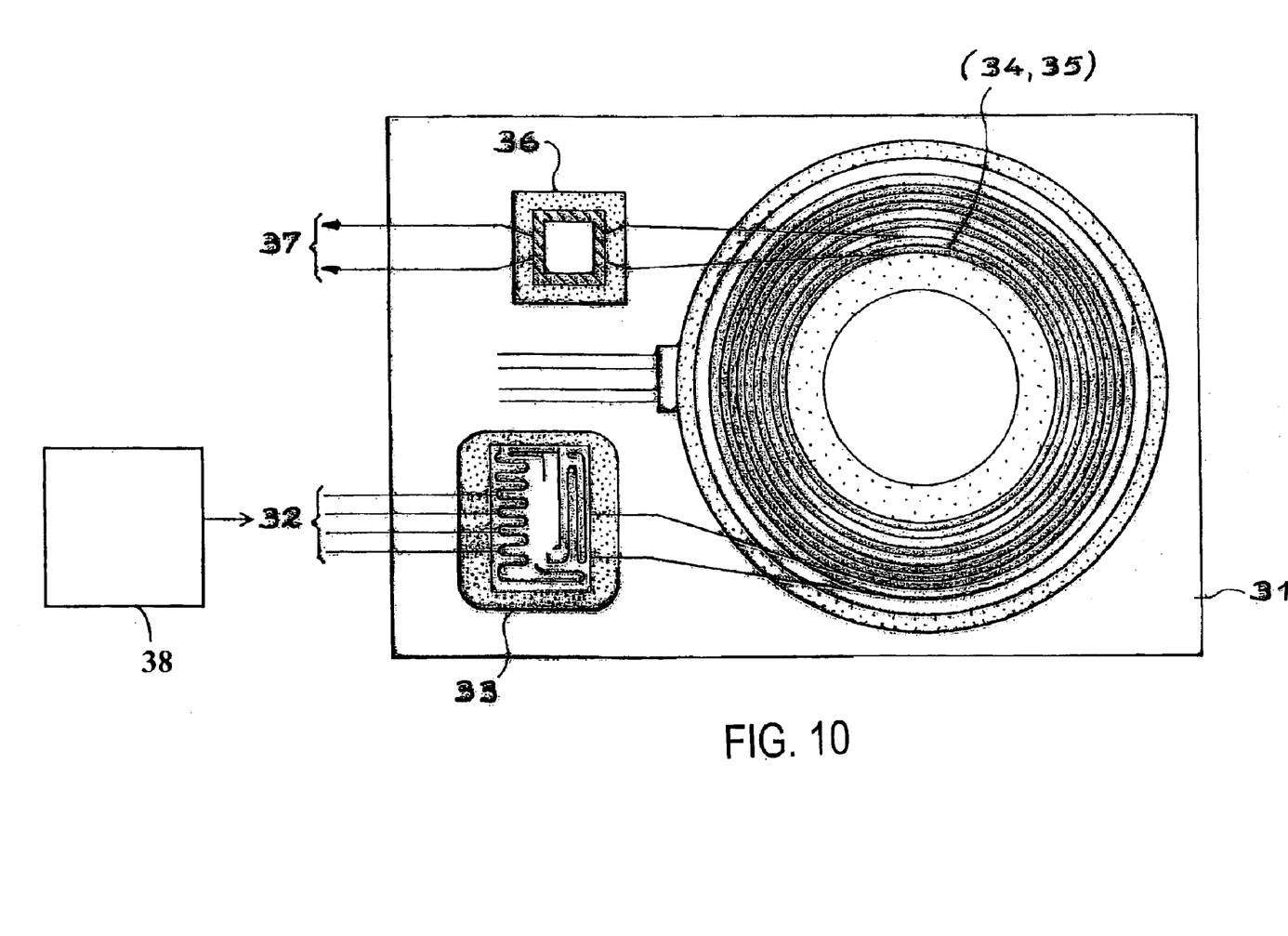
FIG. 10 is a diagrammatic view from above of a microchromatograph capable of being connected to a mass spectrometer by the coupling device according to the invention and further illustrating a preconcentration device upstream from the microchromatograph.

Thus, in FIG. 3, the chromatographic module 31 shown comprises an input 32, an injector 33 connected to an analytic column and to a reference column 34, 35 and, also to a microkatharometer 36 connected to the output 37 of the module. FIG. 10 illustrates a preconcentration device 38 upstream from input 32.

The katharometer (or microkatharometer) discriminates between the gases depending on their thermal conductivity. The principle consists of comparing the thermal conductivity of the pure vector gas in the reference column to that of the gas vector/solute mixtures leaving the analytic column at a given instant t. The measuring principle of the katharometer (or microkatharometer) depends on the Wheatstone bridge.

One of the major properties of this type of detector is the linearity of the response relative to the concentration. The interest of the microdetector is its sensitivity associated to response time, for example 10 milliseconds only: most of the compounds are detected in a concentration range from ppm to 100%.

The "response" of any compound, detected by means of a katharometer, is proportional to the difference in thermal conductivity between this compound and the vector gas. Consequently, it is possible to provide an estimation of the concentration of this compound in a mixture, from the corresponding peak area, nonetheless on the condition that the compound in question has been identified, since knowledge of its thermal conductivity is indispensable for the calculation. Thus, even in the absence of standard mixture, it is possible to carry out an initial estimate of concentrations which remains very acceptable.

Detection, by means of the non-destructive katharometer, and the coupling with a mass spectrometer opens quantitative analysis possibilities for unknown mixtures, without necessarily using corresponding standard mixtures.

According to the invention, the coupling device is also connected to a mass spectrometer.

The mass spectrometer used according to the invention usually comprises an electronic impact source, a quadripole analyser, an electron multiplying detector and the pumping system making it possible to obtain a high vacuum.

The mass spectrometer can be considered, in the case of coupling with the microchromatograph, as a detector with the aim of continuous analysis of the composition of the eluate leaving the microkatharometer.

The mass spectrometer used according to the invention allows rapid sweeping of the mass field, for example 5200 uma/sec, in order to conserve the initial resolution obtained through the chromatography.

The spectrometer registers the mass spectra indiscriminately at a predetermined rhythm. Each spectrum shows a series of mass peaks whose intensities are added up automatically and this sum is called the "total ionic current (TIC)".

The mass spectrometer thus makes it possible to obtain a second chromatogram depending on the variation of the TIC intensity.

Figure 4:
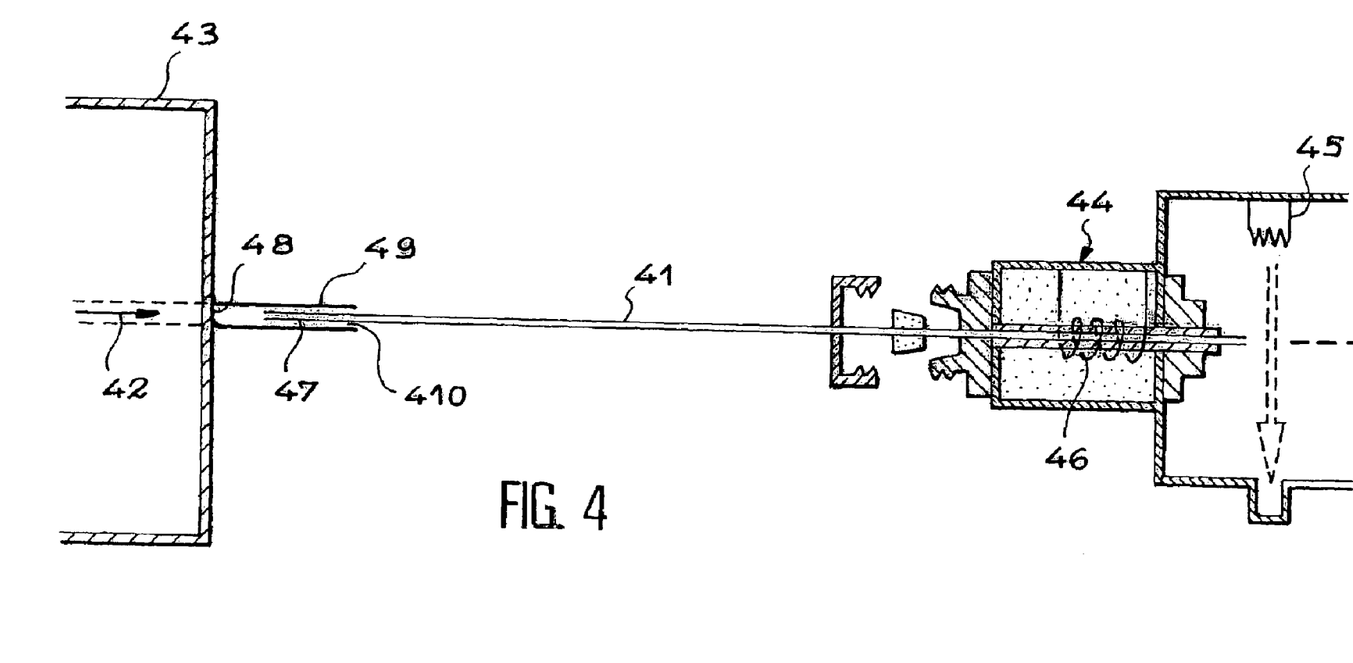
FIG. 4 is diagrammatic cross-section of the coupling device according to the invention.

FIG. 4 shows the coupling device according to the invention.

This coupling device comprises a capillary tube 41 whose length and internal diameter are chosen in such a way that the flow rate circulating inside the tube is approximately equal, or as close as possible, to the flow rate 42 at the output from the microchromatograph 43.

As an example, the internal diameter of the capillary tube can, for example, be 0.15 mm and, in this case, the length of the capillary tube will be close to 1.20 m.

The capillary tube can be made out of any material suitable for this usage. Preferably, the capillary tube is made of deactivated fused silica.

One of the ends of the capillary tube is connected in a sealed manner, through the intermediary of an interface device 44 to the source 45 of the spectrometer under high vacuum ($10^{-5}$–$10^{-6}$ mbar).

The interface device is known to those skilled in the art and already equips many spectrometers on the market: the function of this interface device is to lead the capillary tube to the source of the spectrometer.

The seal relative to the atmosphere is ensured, for example, by means of a ferrule which can be of variable composition (for example graphitised, in wespel-graphite etc.).

According to the invention, the interface device is provided with heating means (46) making it possible to control and adjust the temperature of the interface and thus the capillary tube.

These means can easily be set by those skilled in the art and, for example, can comprise a heating resistance 46.

These heating means for the interface make it possible to adjust and control the flow rate registered by the capillary tube, so that it is the closest possible, by default, to the flow at the output from the chromatograph: the way in which this flow is adjusted through heating the interface will be described in detail below.

The other end 47 of the capillary tube is connected in a slack manner, open to the atmosphere, at the output from the microdetector 48, that is to say that this end of the capillary tube is brought the closest possible to the output from the microdetector 48 but with a slack link, open to the atmosphere.

By the closest, one means that the end of the capillary tube is at a distance of several millimeters from the microdetector.

In FIG. 4, it can be seen that on the microchromatograph side, the capillary tube penetrates a certain distance, for example 5 cm, in a metal tube 49, for example in stainless steel, and is surrounded by it.

This metal tube, with an internal diameter evidently greater than the external diameter of the capillary tube, for example greater by $^1/_{10}$ to $^2/_{10}$ mm than the external diameter of the capillary, is connected to the output of the microchromatograph detector. The gaseous flow of the solute leaving the microchromatograph detector (microkatharometer) at atmospheric pressure, is represented by the arrow 42 in the drawing.

It can thus be seen that an annular space 410 exists between the capillary tube 41, 47 and the metallic tube 49, a space through which atmospheric air can enter. This is the reason why it is a question of a "slack" link open to the atmosphere.

According to the invention, the length and the diameter of the capillary tube are chosen in such a way that the flow circulating inside the tube, fixed by the load loss, is approximately equal or as close as possible to the flow rate at the output from the microchromatograph column.

In order to optimise the diameter of the capillary tube and its length, the inventors have used a specific mounting (see FIG. 5) in which the conditions of circulation of the gaseous flow inside the capillary tube are reproduced: the two ends of the capillary tube are connected in sealed fashion, one of these ends 51 penetrating the source of the mass spectrometer 52 and the other end of the tube being connected to the line 54 through which a helium flow at atmospheric pressure circulates, represented by the arrow 55, through the intermediary of a tapping 56.

Figure 5:
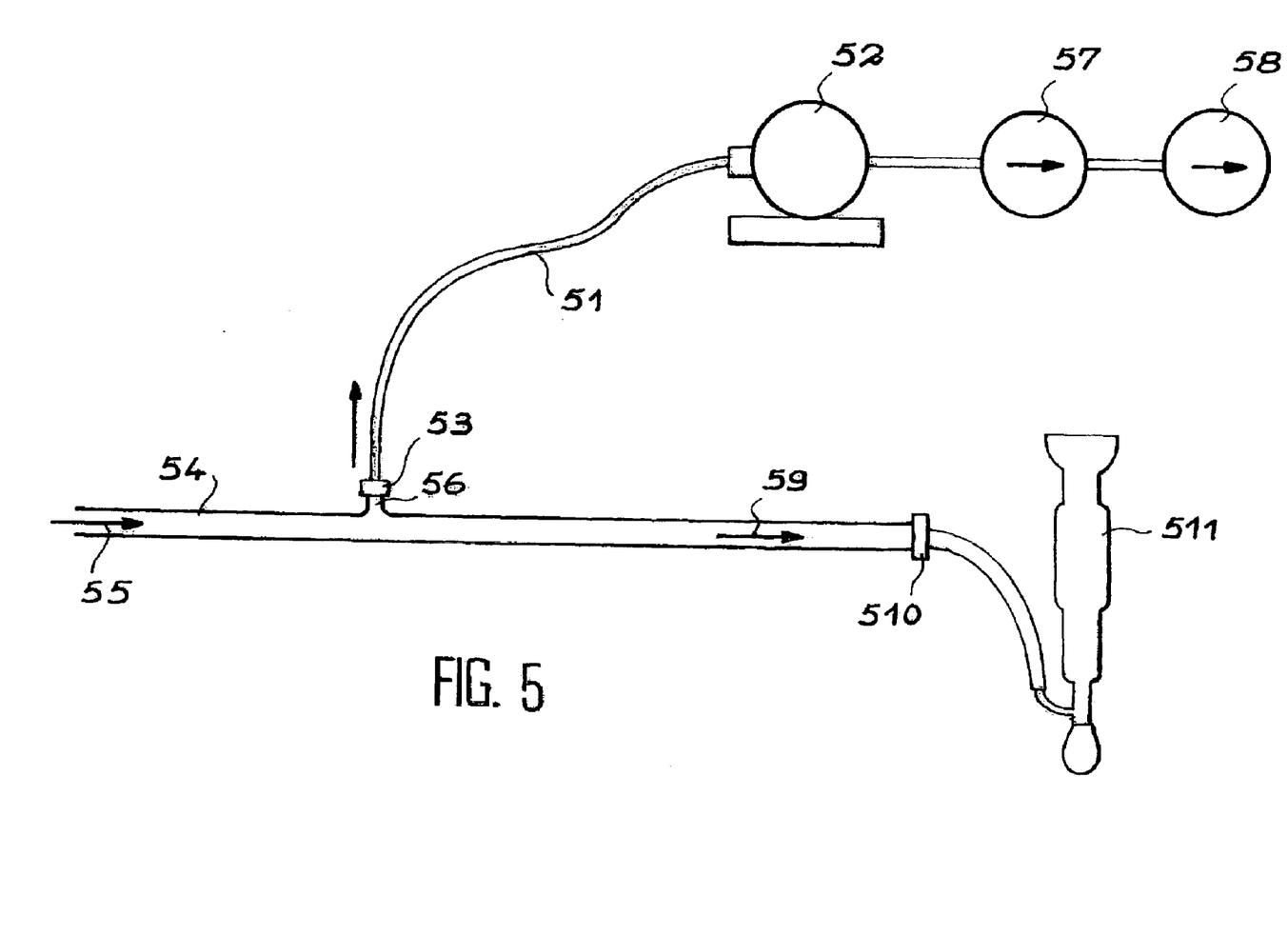
FIG. 5 is a diagrammatic cross-section of the mounting device making it possible to optimise the diameter and length of the capillary tube of the coupling device according to the invention.

In the spectrometer source there is a high vacuum, produced by the secondary pumps 57 and primary pumps 58.

The helium flow rate along the line, upstream from the tapping, is constant: for example about 5 ml/min. While the capillary sucks a certain quantity of flow, the flow rate 59 downstream from the tapping at the output from the line 510 is measured, for example, by a bubble flowmeter 511. The difference in the measurement makes it possible to deduce the flow rate taken by the capillary.

Various tube diameters, for example made of deactivated fused silica, were tested, for example of diameters 0.10 mm, 0.15 mm and 0.25 mm.

The suction flow rate is measured after each successive reduction of the length of the capillary tube, until a value is obtained close to the flow rate measured at the output from the microdetector, that is about 1.5 ml/min.

As an example, it became evident that the best compromise is reached by using the intermediate diameter of 0.15 mm. In fact, a length of 120 cm is then needed to obtain a flow rate close to the optimum. This length makes it possible to preserve the conditions for normal operation of the microkatharometer, that is atmospheric pressure, while keeping a "practical" distance between the two apparatuses.

Use of a lower diameter tube can thus be envisaged. It would enable the length of the capillary tube to be reduced, which tends to preserve the quality of the separation obtained by the chromatographic column.

It is also essential, according to the invention, for the flow rate registered at the output from the microchromatograph to be optimised.

The role of the coupling device and the interface is to create the necessary load loss between atmospheric pressure and the high vacuum in the spectrometer source, while still conserving the separation of species already detected by the microkatharometer. This pressure difference requires the flow through the capillary to be viscous, up to the input of the source and then to become molecular.

A viscous flux is thus to be considered for the micro-CG/device interface-coupling assembly, and consequently the application of the kinetic theory of gases.

The viscosity is therefore defined as being a transport property of gases, together with the thermal conductivity and the diffusion coefficient, all three linked with the agitation of the molecules. The transport coefficients of the gases can in fact be expressed in function of integrals related to the collision dynamics of molecules. And these collision integrals are a function of temperature, such that the speed of transport of a gas in a capillary is lower when the temperature and thus the viscosity of the gas rises.

Thus for a given and constant pressure at the head of a column, the output flow rate from the column of the micro-CG rises corresponding to the lowering of the analysis temperature, in the same way that the flow rate registered by the capillary increases when the interface temperature is close to the ambient temperature. By controlling this latter parameter, that is the interface temperature, the device according to the invention offers the possibility of adjusting the flow rate registered by the capillary very precisely and of bringing this flow rate very close, but slightly by default, to that leaving the chromatographic column.

In real time, observation of the "background noise" of the mass spectrometer enables this adjustment to be precise.

In fact, the relative abundance of the ions detected, of m/z equal to 4, 18, 28 and 32, corresponding respectively to the helium, water, nitrogen and oxygen present, can be visualised in real time.

These ions reflect the quantities of air and of vector gas arriving in the spectrometer source. In the absence of an air leak, the relatives intensities of the peaks m/z=18 ($H_2O$), m/z=28 ($N_2$) and m/z=32 ($O_2$) must be classified in the following order $I_{18}>I_{28}<<I_{32}$. On the other hand, a presence of a majority of $N_2$ over that of $H_2O$ reveals the presence of a leak.

In the case of the "open" coupling according to the invention, a rise in the characteristic peaks for air ($N_2$ and $O_2$) relative to that of water, implies that the flow rate registered by the capillary is slightly too high and is composed of the whole of the flux leaving the detector with an undesirable supplement added, coming from the air present around the non-sealed link.

Therefore, in consequence, the temperature of the interface is adjusted—by acting on its heating means—in such a way as to slightly lower the speed of the flux inside the capillary and to lead the registered flow rate to a level slightly lower than that leaving the microchromatograph, or rather the latter's detector. Inversely, the registered flow rate can be raised if it is too low, by reducing the temperature of the interface, also by acting on the latter's heating means.

Figure 6A:
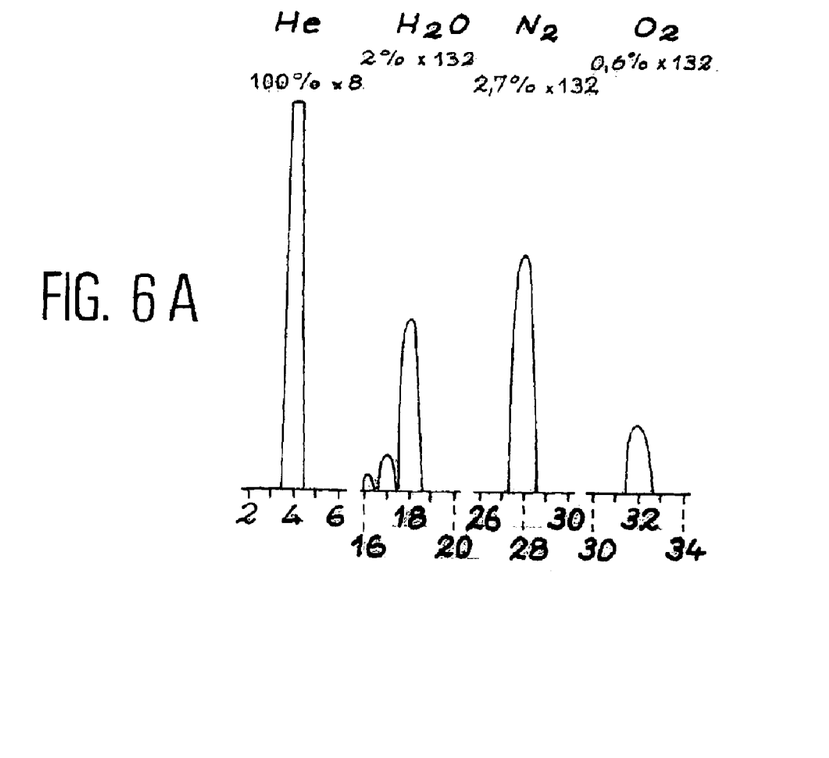
FIGS. 6A and 6B represent the background noise in real time of the mass spectrometer, for an analytic column temperature of 130° C. and respective interface temperatures of 50° C. and 60° C.; the ordinate shows the relative abundance in % and the abscissa shows the ratio m/z.
Figure 6B:
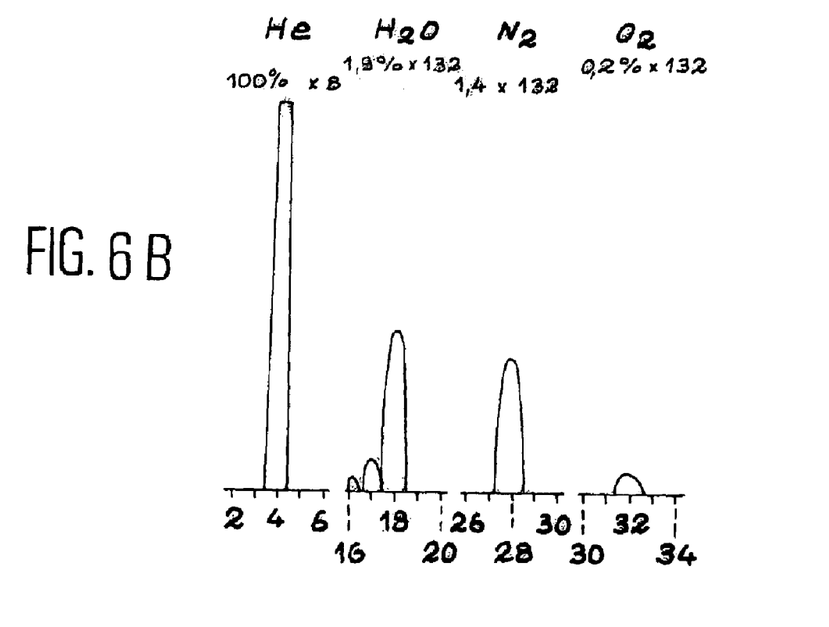
Figure 7A:
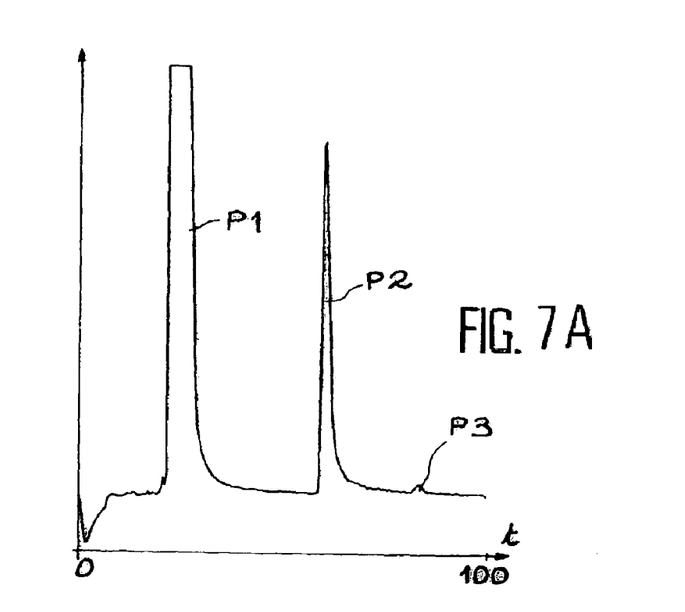
FIGS. 7A, 7B and 7C show, respectively, the chromatogram, the chromatogram based on the total ionic current (TIC) and the mass spectrum obtained during the search for traces of ethylene oxide in surgical pouches.
Figure 7B:
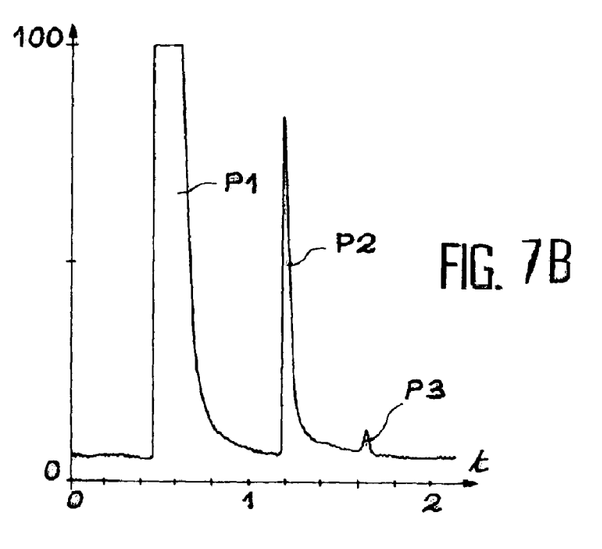
Figure 7C:
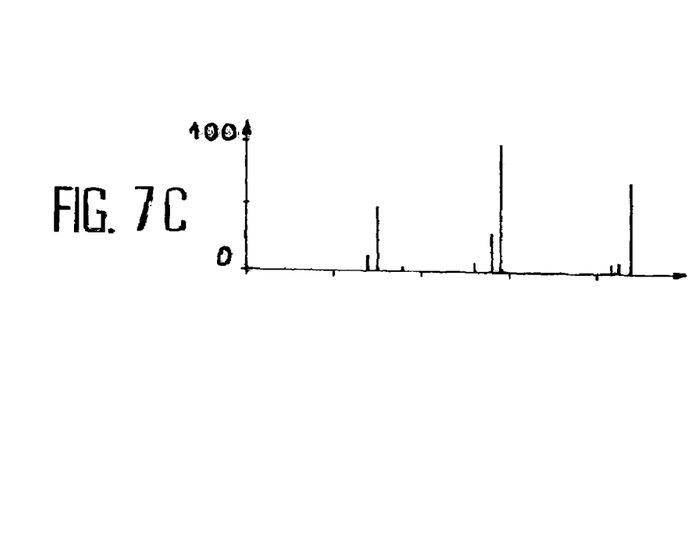
Figure 7D:
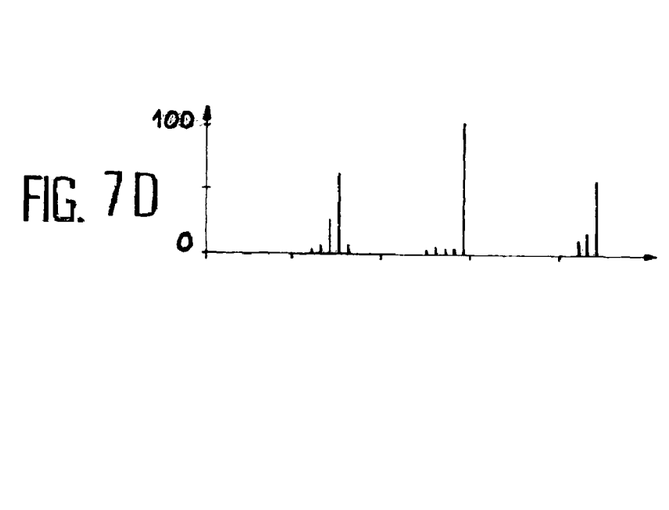
FIG. 7D shows the mass spectrum of the ethylene oxide reference, stored in the spectra data library.

The invention will now be described with reference to the following examples, given for illustrative and non-limiting purposes:

EXAMPLE 1 (FIG. 6)

This example shows the capacity for adjusting the registered flow rate by simple modification of the interface temperature, through the heating means provided in the coupling device according to the invention.

The temperature of the PoraPLOT U® chromatographic column was set at 130° C. for the special needs of an analysis. Under these conditions, the helium flow rate through the column is close to 1.5 ml/min.

FIGS. 6A and 6B make it possible to visualise this "background noise" in real time for the two temperatures chosen (50° C. and 60° C.).

The temperature of the interface is, first of all, set at 50° C. (FIG. 6A). The $N_2$ peak is then higher than that of $H_2O$, which means that the flow rate circulating in the capillary is higher than that at the output from the column and results in dilution of the gaseous flux exiting and parasitic "pollution" by the ambient air.

The temperature of the interface is then raised to 60° C. (FIG. 6B), which has the effect of raising the viscosity of the vector gas and consequently, of reducing slightly the rate of flow inside the capillary tube and bringing the registered flow rate to a level slightly below or almost equal to that leaving the micro-CG detector. This results in a relative abundance of m/z=18 ions (water), in the source which again becomes a majority relative to that of air.

It thus appears that the temperature of the interface, corresponding to a sampling "yield" of 100% for a column temperature of 130° C., is situated between 50 and 60° C. At this temperature, the flow rate registered by the capillary is strictly equal to the output flow rate from the chromatographic column.

This example shows that, thanks to the coupling device according to the invention, the temperature of the interface can thus be optimised for each chromatographic column temperature and an adequate operating field for coupling analysis can be determined under all circumstances: the sensitivity of the katharometer detector is conserved and the optimum operating conditions for the mass spectrometer are safeguarded.

Figure 8A:
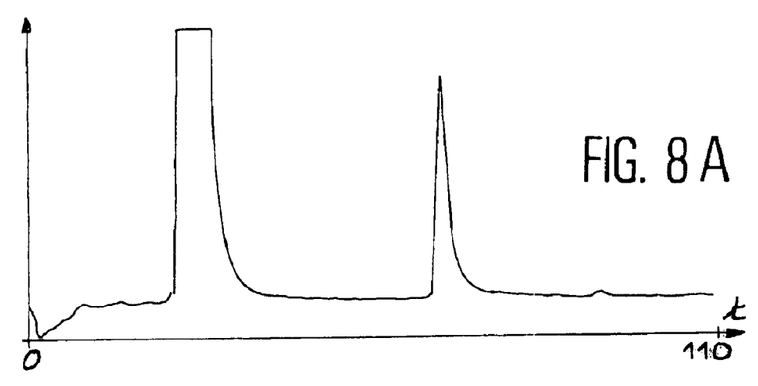
FIGS. 8A, 8B and 8C show the method, called "deconvolution" and representing respectively the chromatogram, the chromatogram based on the ion current m/z=69 and 119 ($C_2F_6$) and the chromatogram based on the ion current m/z=28 and 32 ($O_2+N_2$)
Figure 8B:
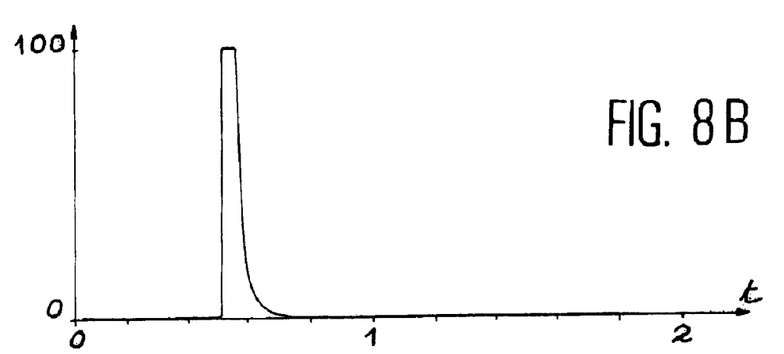
Figure 8C:
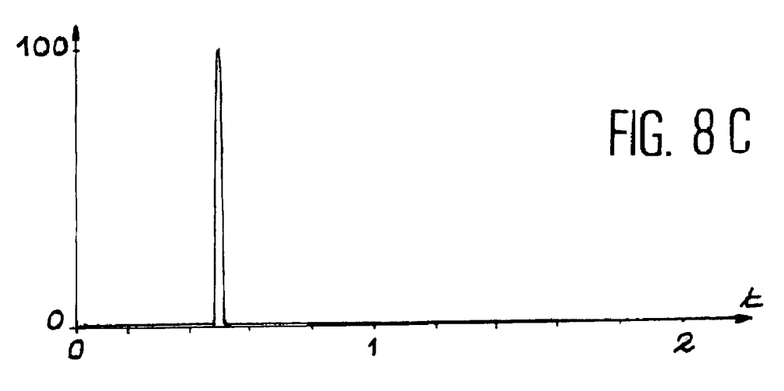

EXAMPLE 2 (FIGS. 7 and 8)

In this example, a device for gas analysis is used, comprising a microchromatograph and a mass spectrometer connected by the coupling device according to the invention to look for traces of ethylene oxide. In fact, certain surgical operations require the use of freon of the $C_2F_6$ type.

This freon is stored at a pressure close to atmospheric pressure in "pouches" or flexible envelopes, previously sterilised by means of processing by ethylene oxide. An international standard defines a tolerated concentration threshold for ethylene oxide, after filling the pouch. Here it is a matter of assaying these traces of sterilizer.

a) Mass Spectrometer

The mass spectrometer used is a mass spectrometer of the quadripole type, provided with a classic interface system. This interface is provided, according to the invention, with a heating system enabling regulation of the temperature from ambient temperature to 200° C.

Before each series of analyses, the mass spectrometer is calibrated. The calibration is generally carried out with masses of 10 to 500 uma, with a sweeping time of 0.4 seconds per spectrum, that is 1225 uma/sec. Afterwards, this spectral acquisition speed constitutes the limit to be respected to remain within the calibration domain.

The parameters of the source of the spectrometer, for coupling analyses as a whole, are as follows:

temperature: 200° C.;

ionisation mode: $IE^+$;

ionisation energy: 70 eV;

ionisation current: 200 µA.

b) Microchromatograph

The microchromatograph, used for coupling, is equipped with two chromatographic modules A and B. The two corresponding capillary columns have the following technical specifications:

| MODULE A | MODULE B |
| --- | --- |
| PoraPLOT ® U Column | A PLOT molecular sieve 5 |
| 4 m, 0.32 mm D.I., 10 µm e.p. | 4 m, 0.32 mm D.I., 30 µm e.p. |
| Vector gas: helium | Usual vector gas: argon |
| Temperature range: 30–160° C. | Temperature range: 30–180° C. |
| Separates light hydrocarbons, alkanes, $CO_2$, $H_2O$, $H_2S$, $SO_2$ . . . | Separates $O_2$, $N_2$, $CH_4$, CO, rare gases, etc. |

Ethylene oxide and freon being separated by the PoraPLOT® U Column, the temperature is set at 110° C., which corresponds to the best compromise between separation and resolution for these two peaks.

Since ethylene oxide is present in trace state in the pouches, the volume injected into the PoraPLOT® U column is set at its maximum value, that is about 15 µl.

The second column (molecular sieve) separates only the constituents of residual air present in the pouch (about 2%); the temperature of the column is thus set at 40° C. and the injected volume is 1 µl, as if it were a classic air assay.

Prior calibration is made in static mode: different air-ethylene oxide mixtures are prepared and then analysed. The resulting calibration curve is a straight line representing the response of ethylene oxide, in function of its concentration from 0 to 100%. This straight line confirms one of the specific properties of the microkatharometer detector: the linearity of response relative to concentration.

c) Coupling Device

The coupling device, according to the invention, is constituted of a capillary tube of diameter 0.15 mm and a length of 120 mm linked, on the one hand, to the output from the microkatharometer, in slack manner, open to the atmosphere and, on the other hand, to the mass spectrometer source, through the intermediary of the interface.

The interface temperature is optimised, after setting the temperature of the chromatographic column, in the way described above.

Optimisation of the interface temperature at 50° C. makes it possible to obtain a quasi-integral sampling of the vector gas flow, without "pollution" by the ambient air.

d) Analyses

The coupling is carried out using a PoraPLOT® U column. The sweeping speed is about six spectra per second, of the mass of 10 to 200 uma. The time required to obtain a spectrum is of the order of 0.16 seconds, which corresponds to an acquisition of 1188 uma/sec.

Current, energy and ionisation mode remain unchanged, together with the source temperature.

e) Results

On the chromatogram resulting from the analysis carried out in the column PoraPLOT® U (FIG. 7A), one can see the peak $P_1$ for air ($O_2+N_2$) co-eluted with freon $C_2F_6$, followed by peaks $P_2$ and $P_3$ for water and ethylene oxide. The retention times $t_R$ are 30, 68 and 93 seconds respectively.

The average surface, measured for ethylene oxide ($P_3$) corresponds, after calibration, to a concentration of 60±4 ppmv.

The chromatogram, based on the total ionic current (TIC) (FIG. 7B), also shows three peaks $P_1$, $P_2$, and $P_3$, corresponding to the constituents of the mixture.

The spectrum of ethylene oxide (FIG. 7C) is obtained by subtraction of the background noise resulting from the residual gases, also ionised.

Comparison of this spectrum (FIG. 7C) with those stored in the data library (FIG. 7D) lead to identification of the product sought, with a similitude index of 82.7% between the two spectra.

f) Comments

The variations of total ionic current build up a chromatogram very similar to that obtained with the microkatharometer. Separation of the different constituents of the mixture by the chromatographic column is preserved during the passage of gaseous flux through the interface.

The difference of retention times between the chromatogram (pCG) and the TIC chromatogram is less than one second.

Ethylene oxide, already seen on the chromatogram, by comparing retention time with that of the standard, is confirmed by mass spectrometry. The spectrum obtained by subtracting the background noise is in fact recognised at 82.7% as being that of the compound sought. This result is very satisfactory, knowing that this identification concerns a compound in trace state.

The ethylene oxide content in the pouch was evaluated at 60±4 ppmV by means of the microkatharometer. The peak area corresponding to this compound makes it possible to announce a detection limit of the order of the ppmv. It should be noted that the surface of this peak, evaluated on the TIC chromatogram, makes it possible to consider that this limit is conserved.

Thus, for the first time, thanks to the device according to the invention, a coupling exists using two detectors whose operational principles differ fundamentally, working on a common sample and whose detection limits are directly comparable.

The appearance of the co-elution of the peaks for air and freon $C_2F_6$ on the chromatogram of FIG. 8A was due to research for traces of characteristic ions. These specific ionic currents (ions m/z=69 and 119 in FIG. 8B; $O_2+N_2$ in FIG. 8C) make it possible to demonstrate the presence of several compounds, where their retention times differ slightly (0.49 minutes in FIG. 8C for air—$N_2$ and $O_2$ non-separated on this column—as against 0.51 minutes for $C_2F_6$ in FIG. 8B). Even though the ionic current is limited to the sum of the two major fragments (69+119), the freon peak evidently seems to be more intense than that of the air. These relative intensities reflect the respective abundance in the pouch (~2% air against $C_2F_6$ in majority).

This well known method of deconvolution can therefore prove to be very useful for coupling analysis of complex mixtures. The search for ion traces makes it possible to confirm the presence of compounds poorly separated by the "coupled" column.

EXAMPLE 3 (FIG. 9)

The aim of this analysis is the identification of two unknown products present in a gaseous mixture in trace state and shown up by a first chromatographic separation carried out on the micro-CG. The mixture comes directly from a furnace used for controlled thermal degradation of polyurethane matrices, at very high temperature and protected from air. The sampling in a gas bottle is carried out during the cooling stage of the furnace under nitrogen flow, the pressure in the bottle being of the order of 850 mbar.

Sampling

Knowing the initial pressure of the sample, this is then brought close to atmospheric pressure by completing the mixture with argon. The inert gas is introduced into the line at a slight over-pressure, the bottle is then connected and the argon expands progressively into the interior until the required pressure is reached. This dilution is then taken into account when making the calculations.

The bottle is isolated and the line placed under vacuum; the argon-sample mixture is thus regulated in order to be analysed.

Analysis Conditions

The temperature of the PoraPLOT U® column is set at 160° C. to separate the two unknown products. The volume injected is about 15 µl.

The sweeping speed is about eight spectra per second, of the mass 10 to 150 uma. Acquisition of a spectrum requires 0.12 seconds, which corresponds to an acquisition of 1167 uma/sec. The current, energy and ionisation mode remain unchanged relative to the preceding example, as does the temperature of the source.

The molecular sieve column can also separate $H_2$ and $N_2$ present in the mixture; to do this the temperature is set at 60° C. and the volume injected is about 1 µl.

Results

Figure 9A:
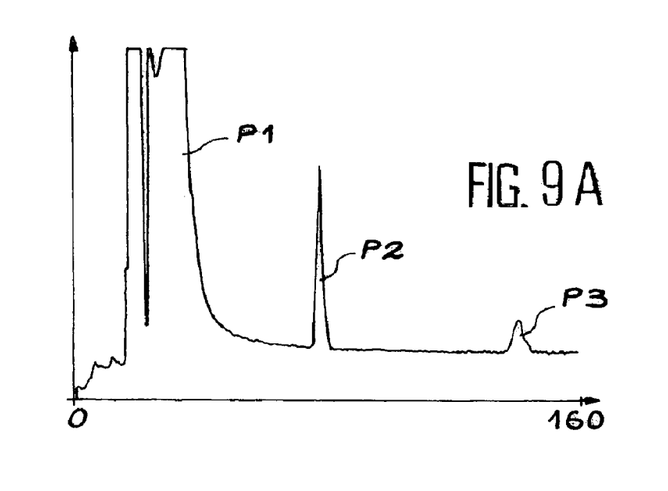
FIG. 9A is a chromatogram (abscissa in time and in seconds) of the unknown mixture.

At the temperature of 160° C., the PoraPLOT U® column separates air, argon, $CO_2$, $NH_3$ and $H_2O$ very poorly (see the wide peak P1 with poor resolution at the head of the chromatogram of FIG. 9A). Next come two peaks $P_1$ and $P_2$ corresponding to the compounds sought, with perfect resolution. Several analyses confirm their presence and the retention times are reproducible, $t_{R2}$=81 and $t_{R3}$=141 seconds respectively.

Figure 9B:
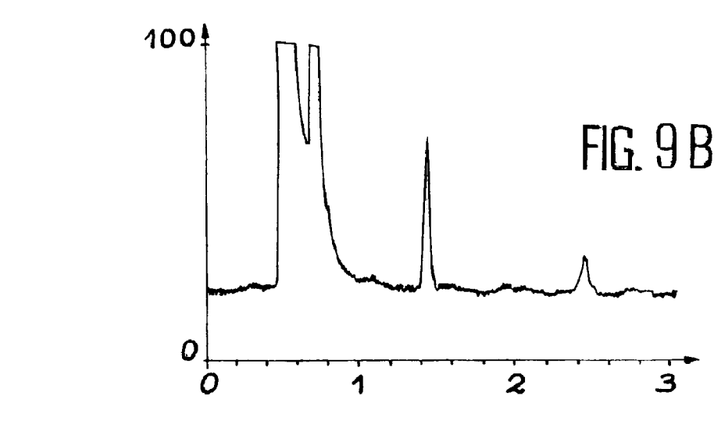
FIG. 9B is the chromatogram based on the total ionic current of this same mixture.
Figure 9C:
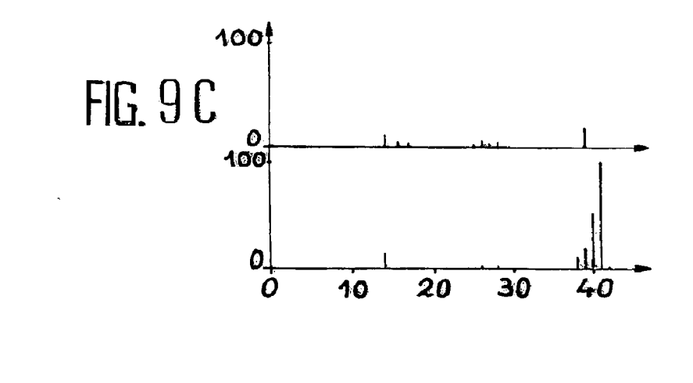
FIGS. 9C and 9D are, respectively, mass spectra of two unknown products detected in the mixture, identified by comparison with the mass spectra stored in the spectra library.
Figure 9D:
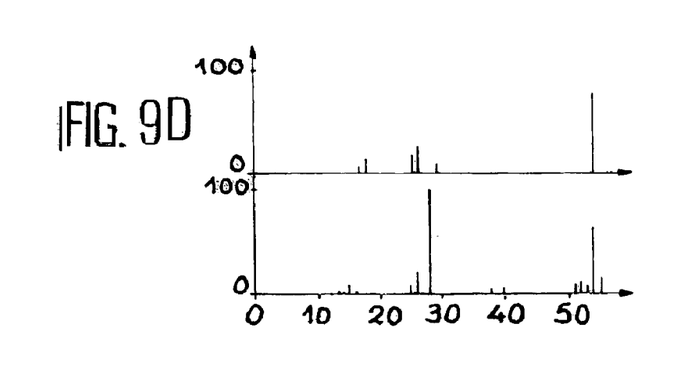

These two compounds are also to be seen on the "TIC" chromatogram of FIG. 9B. The spectra obtained by subtracting the background noise and compared with the data library (FIGS. 9C and 9D) make it possible to identify the corresponding compounds: acetonitrile and propanenitrile. The level of similitude of the spectra gives an identification probability of 90.4% and 73.2%.

Comment

Given the peak surfaces measured by means of the microkatharometer, the overall content for these two compounds, evaluated at a few ppmV, is confirmed.

The mass spectrometer makes it possible to identify these two products with quasi-certainty. The first, at the retention time $t_{R2}$=81 seconds, is recognised at 90.4% as being acetonitrile. The second, at $t_{R3}$=141 seconds, is identified at 73.2% as being propanenitrile. Taking into account the nature and the retention time of the first compound, lighter, and considering the origin of the mixture (cooling under $N_2$ flow and thus the possible formation of C—N bonds), this probability index is sufficient for accepting the proposal.

References

[1] Message, G. M. Practical aspects of gas chromatography/mass spectrometry. John WILEY & Sons ed. 1984, New York.

[2] Henneberg D.; Henrichs U.; Husmann H.; Schomburg G., High-performance gas chromatograph-mass spectrometer interfacing: investigation and optimization of flow and temperature. Journal of chromatography, 1978, 167, 139–147.

[3] Henneberg D.; Henrichs U.; Schomburg G., Special techniques in the combination of gas chromatography and mass spectrometry. Journal of chromatography, 1975, 112, 343–352.

What is claimed is:

1. Coupling device connecting the output of a microchromatograph (µCG) to the input of a mass spectrometer comprising a source under vacuum, said coupling device comprising a capillary tube with one end connected in sealed fashion to the source under vacuum of the mass spectrometer through the intermediary of an interface device, and with the other end connected to the output of the microchromatograph, in slack fashion, open to the atmosphere; the length and the diameter of the capillary tube being chosen such that the flow rate inside the capillary tube is very close to the flow rate at the output from the microchromatograph; the interface device being, furthermore, provided with heating means for very precise adjustment of the flow rate registered by the capillary.

2. Device according to claim 1, in which the temperature of the interface is adjusted in such a way that the flow rate registered by the capillary tube is very close or equal to the flow rate at the output from the microchromatograph.

3. Device according to claim 1, in which the relative intensity of the peaks is compared, on the one hand for water and, on the other hand for nitrogen and/or oxygen from the mass spectrometer and action is taken in consequence on the means for heating the interface in order to raise or lower the temperature of the latter, and to reduce or increase respectively the flow rate registered by the capillary tube.

4. Device according to claim 1, in which the heating means make it possible to adjust the temperature of the interface from ambient temperature to 200° C.

5. Analysis device comprising a microchromatograph and a mass spectrometer, the output from the microchromatograph being connected to the input of the mass spectrometer by a coupling device according to claim 1.

6. Analysis device according to claim 5, provided furthermore, upstream from the microchromatograph, with a pre-concentration device depending on an adsorption followed by a thermo-desorption.

* * * * *